(12) United States Patent
Vija et al.

(10) Patent No.: US 11,524,178 B2
(45) Date of Patent: Dec. 13, 2022

(54) INTERNAL DOSE TOMOGRAPHY (71) Applicant: Siemens Medical Solutions USA, Inc., Malvern, PA (US)

(72) Inventors: Alexander Hans Vija, Evanston, IL (US); Michal Cachovan, Baiersdorf (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 480 days.

(21) Appl. No.: 16/845,316

(22) Filed: Apr. 10, 2020

(65) Prior Publication Data
US 2021/0106848 A1    Apr. 15, 2021

Related U.S. Application Data

(60) Provisional application No. 62/912,855, filed on Oct. 9, 2019.

(51) Int. Cl.
| | |
|---|---|
| *A61N 5/10* | (2006.01) |
| *A61B 6/03* | (2006.01) |
| *G06T 7/00* | (2017.01) |
| *G06T 11/00* | (2006.01) |

(52) U.S. Cl.
CPC ............ *A61N 5/1071* (2013.01); *A61B 6/037* (2013.01); *A61N 5/1075* (2013.01); *G06T 7/0012* (2013.01); *G06T 11/008* (2013.01); *A61N 2005/1021* (2013.01); *A61N 2005/1074* (2013.01); *G06T 2207/10072* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 7,668,662 | B2 * | 2/2010 | Kroll | A61K 51/1069 424/1.49 |
| 8,577,103 | B2 | 11/2013 | Vija | |
| 8,675,936 | B2 | 3/2014 | Vija | |
| 9,171,353 | B2 | 10/2015 | Vija | |
| 9,332,907 | B2 | 5/2016 | Vija | |
| 9,364,192 | B2 | 6/2016 | Vija | |
| 2011/0060602 | A1 * | 3/2011 | Grudzinski | G16H 20/40 705/2 |
| 2014/0193336 | A1 * | 7/2014 | Rousso | A61B 6/503 600/431 |
| 2019/0168029 | A1 | 6/2019 | Cachovan | |

OTHER PUBLICATIONS

M., S., Stabin M. The case for patient-specific dosimetry in radionuclide therapy. Cancer Biother Radiopharm. 2008;23(3). 2008.
(Continued)

*Primary Examiner* — Hoon K Song (57) ABSTRACT

Parameterized model reconstruction is used for internal dose tomography. The parameterized model, solved for within the reconstruction, models the dose level and may account for diffusion, isotope half-life, and/or biological half-life. Using the detected emissions from different scans (e.g., from different scan sessions in a given cycle) as input for the one reconstruction, the parameterized model reconstruction determines the biodistribution of dose at any time.

20 Claims, 5 Drawing Sheets

(56) References Cited

OTHER PUBLICATIONS

Stabin, M., Nuclear medicine dosimetry. Physics in Medicine and Biology, 2006. 51: p. R187-R202.
Stabin, M. and A.B. Brill, Physics Applications in Nuclear Medicine: 2007. Journal of Nuclear Medicine, 2008. 49(2): p. 20N-25.
Stabin, M.G. and J.A. Siegel, Physical Models and Dose Factors for Use in Internal Dose Assessment. Health Physics, 2003. 85(3): p. 294-310.
Stabin, M.G., R.B. Sparks, and E. Crowe, OLINDA/EXM: The Second-Generation Personal Computer Software for Internal Dose Assessment in Nuclear Medicine. Journal of Nuclear Medicine, 2005. 46(6): p. 1023-1027.
Watson, E.E., M.G. Stabin, and J.A. Siegel, MIRD formulation. Medical Physics, 1993. 20(2): p. 511-514.
Extended European Search Report received in corresponding European Patent Application No. 20178318.0, dated Oct. 30, 2020.
Götz, Theresa Ida:; "Technical Report: Time-Activity-Curve Integration in Lu-177 Therapies in Nuclear Medicine"; arxiv.org; Cornell University Library; XP081442245.
Huizing, Daphne Merel Valeria et al:; "Dosinometry methods and clinical applications in peptide receptor radionuclide therapy for neuroendocrine tumours: a literature review"; EJNMMI Research; Biomed Central Ltd; vol. 8; No. 1; pp. 1-11.

* cited by examiner

INTERNAL DOSE TOMOGRAPHY

BACKGROUND

The present embodiments relate to emission tomography or nuclear imaging. Conventional nuclear imaging begins with the introduction of a radiopharmaceutical or radiotracer into a patient. The radiopharmaceutical emits gamma rays (in the case of single-photon-emission-computer-tomography (SPECT) imaging) or positrons that annihilate with electrons to produce gamma rays (in the case of positron-emission-tomography (PET) imaging). A detector system located outside the patient detects the emitted gamma rays and reconstructs images based on the detected emissions.

According to theranostics, the radiopharmaceutical is used as a therapeutic agent. Emitted radiation applies a therapeutic dose to tracer-targeted tissue within the volume. Multi-cycle theranostics involves the introduction of tissue-dosing radiopharmaceuticals at multiple successive procedures (i.e., cycles) occurring at different times (typically different days). Nuclear images are acquired at multiple timepoints (e.g., over a day or two) during each cycle in order to monitor the distribution and amount of dose over time. The generic function of uptake and washout of the radiopharmaceutical is a shark-fin like function, which is not known for an individual and depends on the specific individual and radiopharmaceutical injected.

Internal dosimetry, such as medical internal radiation dose (MIRD), is the estimation of energy deposited to tissue due to uptake of the radioactive substance in the patient. The common method is estimation from two-dimensional (2D) imaging, which suffers from poor accuracy, or from three-dimensional (3D) tomography, which is time consuming. In a more accurate approach, U.S. Published Patent Application 2019/0168029 ("Multi-Cycle Theranostics with Dosimetry and Dose Error Estimation") teaches separate multi-modal quantitative SPECT reconstructions for computing voxel-based quantitative uptake (Bq/ml) at each of multiple time points to then determine dose. The approach may be complex and/or time consuming.

SUMMARY

By way of introduction, the preferred embodiments described below include methods, systems, instructions, and computer readable storage media for internal dose tomography. Parameterized model reconstruction is used. The parameterized model, solved for within the reconstruction, models the dose level and may account for diffusion, isotope half-life, and/or biological half-life. Using the detected emissions from different scans (e.g., from different scan sessions in a given cycle) as input for the one reconstruction, the parameterized model reconstruction determines the biodistribution of dose at any time.

In a first aspect, a method is provided for internal dose tomography. First and second sets of emissions are detected from a patient at first and second timepoints of a first radiopharmaceutical therapy cycle. Tomographic, parametric model reconstruction from the first and second sets of emissions is performed. The tomographic, parametric model reconstruction solves for a model of pharmaceutical kinetics as part of the reconstruction. Dose is determined based on the model of pharmaceutical kinetics from the parametric model reconstruction. The dose is displayed.

In one embodiment, spatio-temporal inconsistent emissions are detected with a single photon emission computed tomography scanner. The detection at the first and second timepoints of the first radiopharmaceutical therapy cycle includes detection from different scans separated by at least one hour after a first application of a radiopharmaceutical and before a subsequent application of the radiopharmaceutical. The reconstruction may be from emissions detected at additional time points, such as from a second radiopharmaceutical therapy cycle.

In another embodiment, performing the reconstruction includes performing with the parametric model for one segment of tissue of the patient with the one segment identified from extra-modal or intra-modal information; solving for the model as a dynamic variation for wash-in and wash-out of a radiopharmaceutical; and/or solving for the model as a dynamic variation for isotope and biological half-lives.

In some embodiments, the dose is determined as a mean for a volume of a structure of interest. The dose may be determined directly from the reconstruction of the dose as part of the performing the reconstruction.

In further embodiments, calibration for tissue density and isotope is used. The results of the calibrating are used in the reconstruction and/or dose determination. In another further embodiment, uncertainty for the dose is calculated. The dose and the uncertainty are displayed. Motion correction, partial volume estimation, and/or other reconstruction or tomography processes may be performed.

In a second aspect, a method is provided for dose estimation from radiopharmaceutical therapy. Quantitative uptake and dose distribution are parametrically estimated as part of parametric reconstruction from emissions of multiple timepoints corresponding to separate scans of separate imaging sessions. An image of the dose distribution and quantitative uptake is generated.

In other embodiments, the parametric estimation includes estimation with a model of tracer dynamics for biological dose efficacy; reconstructing with different parametric models for different types of tissue; and/or estimating based, in part, on dose calibration. For the different models for different tissues embodiment, the generated image may be generated with the image showing average quantitative uptake by type of tissue.

In a third aspect, a medical imaging system is provided. An emission tomography system is configured to detect emissions from the patient during different imaging sessions. The patient is subjected to therapy from a radiotracer during the different imaging sessions. An image processor is configured to reconstruct a biodistribution of the radiotracer by fitting a parametric model of biological half-life of the radiotracer to the detected emissions and to determine a dose from the fit parametric model. A display is configured to display the dose.

In another embodiment, the parametric model includes radiation transport and ionizing radiation energy deposition by tissue type. In yet another embodiment, the image processor is configured to reconstruct the biodistribution based, in part, on a calibration for an isotope of the radiotracer.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In U.S. Published Patent Application 2019/0168029, the voxelized uptake is computed for each of different timepoints. A dose model of the time activity curve is fit to the uptakes over time to compute the dose (e.g., energy/mass or J/kg (Gy)). The dose function, D, is a function of time and is different from activity, A=Bq. While the voxelization in 3D is advantageous over the clinical practice of 2D or 3D MIRD, it is suboptimal due to overly reliance on human interpretable intermediate images, which may be reconstructed sub-optimally for dose estimation.

For internal dose tomography, a different approach uses the available data from the 1 . . . N timepoints to describe a dynamic process for tissue segments (zones) of interest and specifying what moment of the spatial distribution is desired. The 1 to N timepoints are used in one reconstruction to parametrize tracer dynamics and dose distribution also with respect to biological dose efficacy. In order to provide a reliable and quantitative measure of dose induced to relevant organs and tissues, a biological model is estimated as the parameterized model of the reconstruction and included into the dose computation. The reconstruction uses a parametric estimation of quantitative uptake along with dose distribution within the reconstruction. The accuracy of the calibrated quantitative dose values may be estimated within the reconstruction. This internal dosimetry is used to oversee and drive personalized therapy decisions.

Instead of computing the quantitative uptake at each time point, the tomographic data from multiple (e.g., all) available time points is used to directly reconstruct the dose. For example, a spatio-temporal inconsistent SPECT, where the tomographic dwell time the dwell T_D<<T_R (residence time of the radiopharmaceutical) and assuming that the activity is constant or only slowly changing over T_D as compared to T_R, measures at the different timepoints. The dose in the target volume is reconstructed directly in a parametric approach. In this parametric reconstruction approach, the error propagation is seamless, and the noisy voxels at the later times are naturally stabilized. This parametric approach provides a fit model of dose, that may extend to temporal consistent SPECT systems and T_D<<or just <than T_R. Quasi static uptake is not assumed as the model as fit in the reconstruction provides for dose variation over time.

Figure 2:
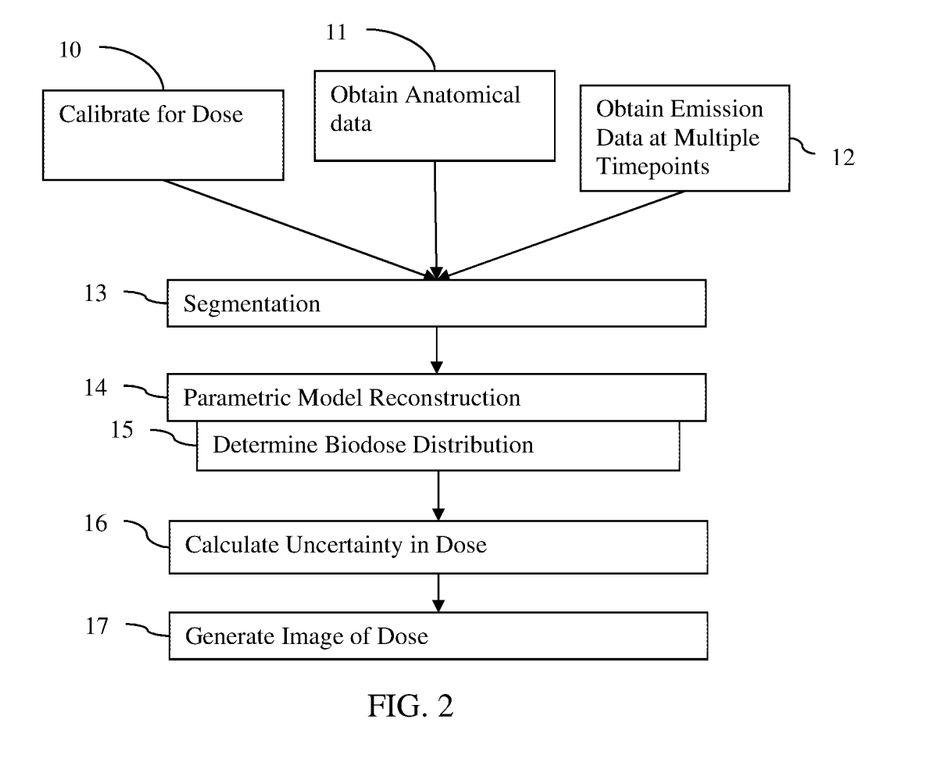
FIG. 2 is a flow chart diagram of one embodiment of a method for internal dose tomography.

FIG. 2 shows one embodiment a method for internal dose tomography using an emission tomography system. The method provides for dose estimation from radiopharmaceutical therapy. Parametric model reconstruction is used. Emissions from different time points are used in the parametric model reconstruction with a model of dose dynamics, such as including dose distribution, isotope half-life, biological half-life, and/or other pharmaceutical kinetics. The emissions over time as measured by the emission tomography system are used to solve for dose within the reconstruction.

Figure 5:
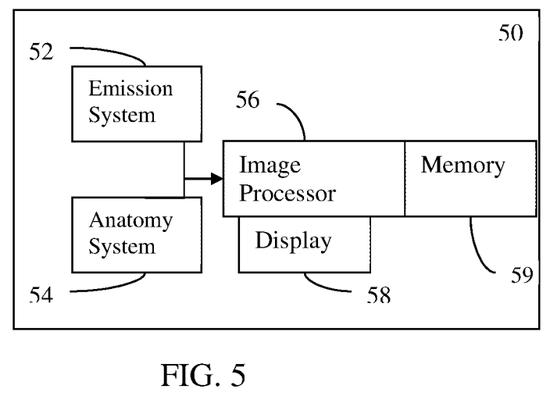
FIG. 5 is a block diagram of one embodiment of a multi-modality system for internal dose tomography.

The method of FIG. 2 is implemented using the system of FIG. 5, an image processor, a computer, a CT scanner, an MR scanner, a SPECT imager, a PET imager, a server, and/or another device. For example, a CT or MR scanner performs act 11, and a SPECT or PET imager performs act 12. A computer or image processor of one of the scanners or imagers performs acts 10 and 13-17.

The method is performed in the order shown (numerical or top to bottom), but other orders may be used. For example, acts 11 and 12 are performed simultaneously or in any sequence.

Additional, different, or fewer acts may be provided. For example, act 11 is not performed, such as where the detected emissions are used for intra-modality imaging and segmentation. As other examples, motion correction, partial volume correction, and/or uncertainty estimation acts are included. As another example, the generation of the image in act 17 is not performed. In another example, acts for configuring for scanning a patient and/or for planning therapy are included.

In act 10, the emission tomography system is calibrated. A phantom with a known dose and isotope is used. The emission tomography system detects emissions from the phantom. The phantom may emulate the density of particular tissues, so that the dose calibration is performed for different tissue densities. Alternatively, the measured dose from the known source is altered to account for known tissue density information, providing calibrated dose by tissue type. The calibration provides an adjustment or weighting for measured uptake for a given emission tomography or class of emission tomography systems. The measured uptake is adjusted to be more accurate based on the calibration. Different calibration may be provided for different tissue density and/or isotope.

In act 11, an imaging modality different than emission tomography obtains anatomical information for the patient. Any imaging modality may be used, such as computed tomography (CT), magnetic resonance (MR), or ultrasound. The modality scans the patient to provide anatomical information about the patient in a same region from which emissions are detected by emission tomography.

Where zonal reconstruction is used to provide higher resolution reconstruction, the measures of emissions are separated into zones for the reconstruction. The anatomical information may be obtained for creating the zones. The zones represent locations within the examined patient and are derived from the anatomical information. Multimodal reconstruction may improve the image quality and/or reduce the acquisition time of the emission imaging process by considering the zonal information in the reconstruction.

The anatomical data is used for extra-modality information (EMI) reconstruction. The emission tomography system detects emissions from the patient. The anatomy imaging system detects signals from the patient based on x-ray, magnetic resonance, or ultrasound scanning. The anatomy information is used to create a p-map for attenuation correction and a zone map for zonal or multimodal reconstruction. The detected emissions are reconstructed using the p-map and the zonal reconstruction map. The detected emissions are used to reconstruct dose into object or image space representing dose distribution in the patient. Alternatively, zonal reconstruction is not provided, so the zone map for zonal reconstruction is not created.

In act 12, multiple sets of emissions from a patient are detected at multiple timepoints. The timepoints are during a given radiopharmaceutical therapy cycle, such as after ingestion or injection and before a subsequent ingestion or injection for another cycle. The timepoints may alternatively be spread over two or more cycles.

Separate scans are used for each of the timepoints. A given timepoint may be a period associated with a given imaging session. Each session corresponds to an appointment and/or occasion where a patient arrives, is imaged, and departs. Separate timepoints are separate periods for imaging, where the separation is by many minutes, such as at least one or more hours. Emissions are detected, such as with a complete SPECT or PET scan, for each of the timepoints.

Figure 1:
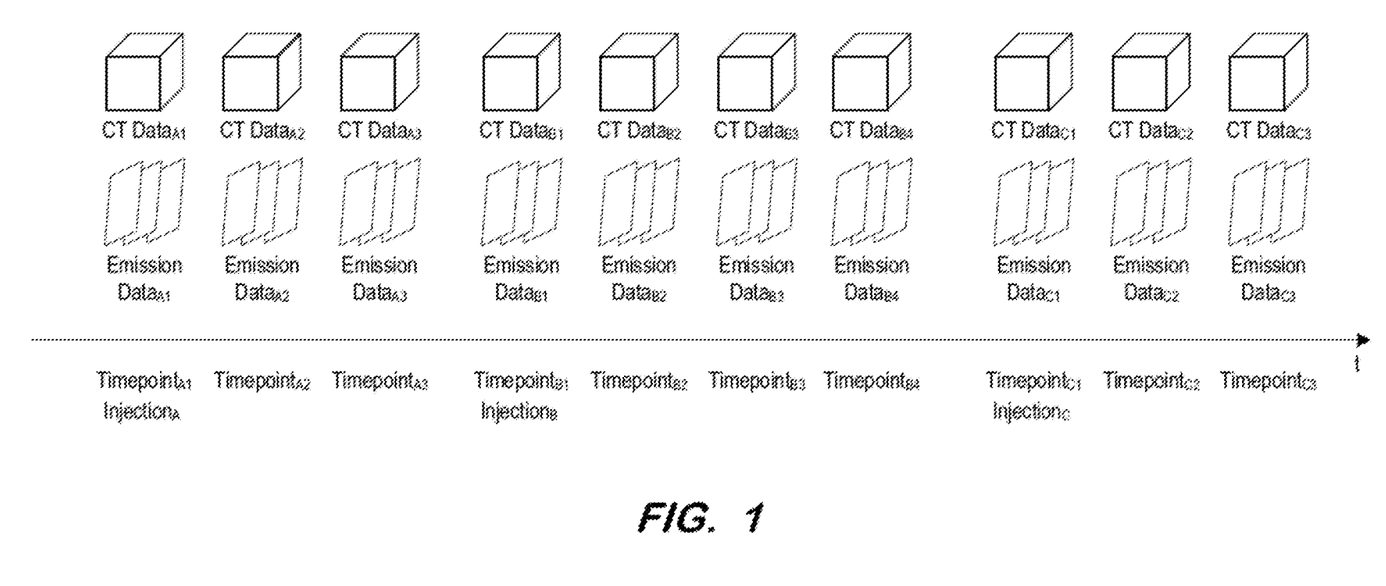
FIG. 1 illustrates multi-cycle theranostics according to some embodiments.

The detection during different imaging sessions provides for detection of spatio-temporal inconsistent emissions with a SPECT or PET scanner. FIG. 1 illustrates a theranostics process according to some embodiments. The illustrated process includes three cycles spaced over a number of days. Embodiments are not limited to any particular number of cycles or to any particular time period between cycles.

Each cycle includes an injection of radiopharmaceutical at a first timepoint and acquisition of images at several subsequent timepoints. Any suitable therapeutic radiopharmaceutical may be employed and may be introduced into a patient volume via injection, ingestion, and/or any other suitable process. Moreover, the number of imaging timepoints is not limited to any particular number and need not be the same for each cycle.

According to the illustrated example, tomographic nuclear emission data and computed tomography data are acquired at each timepoint. Emission data may comprise a plurality of sets of two-dimensional emission data generated by an emission imaging system during a scan of a body. As described above, such a system may comprise a SPECT system, a PET system, or another type of nuclear imaging system that is or becomes known.

In some embodiments, computed tomography data is not acquired at each timepoint. The processes described herein may use computed tomography data from a prior study or computed tomography data that is acquired once per cycle, for example. Embodiments are not limited to the two imaging modalities of FIG. 1, or to only two modalities. Embodiments may include acquisition of tomographic SPECT data and magnetic resonance (MR) data at each timepoint, for example.

The emission data is obtained from detection, from data transfer, or from memory. An emission tomography system provides the emission data directly by detecting from a patient or indirectly by transfer or loading from a previous detection. The activity concentration in a patient having received a radiotracer or radiotracers is determined as part of reconstruction by the emission tomography system. After ingesting or injecting the radiotracer or tracers into the patient, the patient is positioned relative to an emissions detector, and/or the detector is positioned relative to the patient. Emissions from the radiotracer within the patient are detected over time. A collimator in front of the detector limits the direction of photons detected by the detector, so each detected emission is associated with an energy and line or cone of possible locations from which the emission occurred. The lateral position of the line or cone relative to the detector may likewise be determined.

Raw emission data or preprocessed data is provided for multi-modal or other reconstruction. The multimodal reconstruction may use a system matrix or projection operators to describe the properties of the emission tomography imaging system to iteratively improve a data model of an image object representing the dose. The image object may then be displayed using volume rendering or other imaging techniques.

The image object, which is defined in an object or image space, is a reconstruction from the emission data measured in a data space. The object space is the space in which the result of the image reconstruction is defined and corresponds, for example, to the 3D volume (i.e., field-of-view or "FOV") that is imaged.

The anatomy data and emission data are co-registered to provide registration. For example, anatomical CT data is co-registered with a preliminarily reconstructed image object. In other embodiments, a multi-modality system is used, allowing the emission data and the anatomy data to be obtained with the patient in the same position. The spatial relationship of the emission tomography system to the anatomy imaging system is known or calibrated.

In act 13, an image processor segments locations representing an organ, tumor, and/or other types of tissue based on the anatomical data. The segmentation identifies locations representing an object or objects of interest in the patient, such as a specific organ. The group of locations representing the same object is a zone. A tissue-based zone map is generated. For example, the voxels or locations representing a liver are identified. Any organ, part of an organ, type of tissue, and/or another object in a patient may be segmented.

In zonal reconstruction, CT, MR, or other data representing the patient (e.g., μ-map or attenuation) is used to identify one or more zones. A zone need not be an enclosed area. The zone is continuous or discontinuous. The zones define spatial regions associated with a given grouping of one or more types of tissue. One zone may represent a target organ or target tissue of the biomarker used for the functional image. Any number of zones may be identified. Each zone is defined by locations in the volume at which that type of tissue occurs.

The zone for the organ or object of interest provides a segmentation for that object. To segment the object-of-interest, the zone map may be used to identify the locations for a given zone or object. Alternatively, the CT or other data is segmented to define the locations for the object, such as the liver. Any segmentation may be used, such as template matching, thresholding, and/or machine-learnt classification.

In one embodiment, both the anatomical data and the emission data are used for segmentation. The anatomical data is used to identify locations of the object as an extra-modality imaging (EMI) segmentation. The emission data is used to identify tumors or lesions within the object as an intra-modality imaging (IMI) segmentation. An initial reconstruction from the emission data shows locations of higher (e.g., above a threshold) or other abnormal activity. After any low pass filtering and/or clustering, locations corresponding to one or more tumors or relatively higher activity concentration are identified. The segmentation includes locations of the object and excludes locations in the object that are tumors or lesions. Other segmentation using other data may be used. Just EMI or just IMI segmentation may be used.

In act 14, the image processor performs tomographic, parametric model reconstruction from the multiple sets of emissions. The detected emissions form projections, which may be tomographically computed to represent two- or three-dimensional distribution by reconstruction. The reconstruction uses emissions detected from different directions or camera locations in each set of emissions. The reconstruction uses the sets of emissions from different timepoints or complete scans for parametric reconstruction. Emission data not only from one timepoint but also from multiple or all available timepoints of a therapy cycle or cycles may be used.

An augmentation to multi-cycle dose computation and tumor/tissue radiation dose response could be modelled. The reconstruction includes a parametric model of pharmaceutical kinetics, such as diffusion, isotope half-life, biological half-life, and/or another characteristic of change over time in dosage being applied from the radiotracer. Monte Carlo or dose kernels may be used in one embodiment to model emission probability and/or interaction for dose. In determining the distribution of the radiopharmaceutical from the emissions at different time points, values of the model parameters of the parametric model are solved, providing a patient-specific model indicating dose for any time and/or total dose for the locations of the distribution. As an example, a 2-compartemental model is encapsulated in a set of linear differential equations, whereby the k12, . . . are kinitic parameters for moving from compartment 1 to compartment 2. Generally, the compartment can be a voxel or a volume of interest (VOI), like an organ (e.g., tissue that has common properties at some spatial scale). In one embodiment, the reconstruction parametrically estimates quantitative uptake and dose distribution as part of parametric reconstruction from emissions of multiple timepoints corresponding to separate scans of separate imaging sessions. Parametric modelling is performed within reconstruction employing information from both the image domain and projection domain.

The reconstruction estimates the delivered dose or radiation energy deposition using a model of tracer dynamics for biological dose efficacy. The tomographic, parametric model reconstruction solves for the model of pharmaceutical kinetics as part of the reconstruction. The model represents dynamic variation for wash-in and wash-out of a radiopharmaceutical. For example, the model includes for one or two diffusion levels. The model may include dynamic variation for isotope and/or biological half-lives. The isotope half-life may be known, so the model is used to solve for the biological half-life, which is influenced by the tissue of the patient. Tomography of spatial estimation of activity is thus replaced by a tomographic consistent parametric fit of a slow dynamic wash-in and wash-out process or another model of dose. The emissions from different timepoints are used in solving during or as part of reconstruction. The reconstruction output provides a tracer distribution as well as a fit dose model, allowing determination of dose at any given time.

The tomographic reconstruction iteratively fits the detected emissions to a distribution of the radiopharmaceutical in object or image space. Iterative optimization is applied to find the distribution that best fits the measured emissions. Backward and forward projection from the detection space and the object space are used as well as any modeling, such as the system model for the emission tomography system (e.g., detector sensitivity) and the parametric model for kinetics of the radio tracer (e.g., diffusion in two directions (e.g., k1 and k2) with decay). In an iterative optimization, a model of the emission tomography system is used to forward project measurements to object space, and residuals are back projected for correcting a data model for the next iteration. Any type of reconstruction may be provided, such as provided in U.S. Pat. Nos. 9,171,353; 9,332,907; 8,675,936, and/or 8,577,103. In one embodiment, multi-modal reconstruction is used where the reconstruction uses the segmentation or segments from act 13 in determining the distribution of the emissions.

Figure 3:
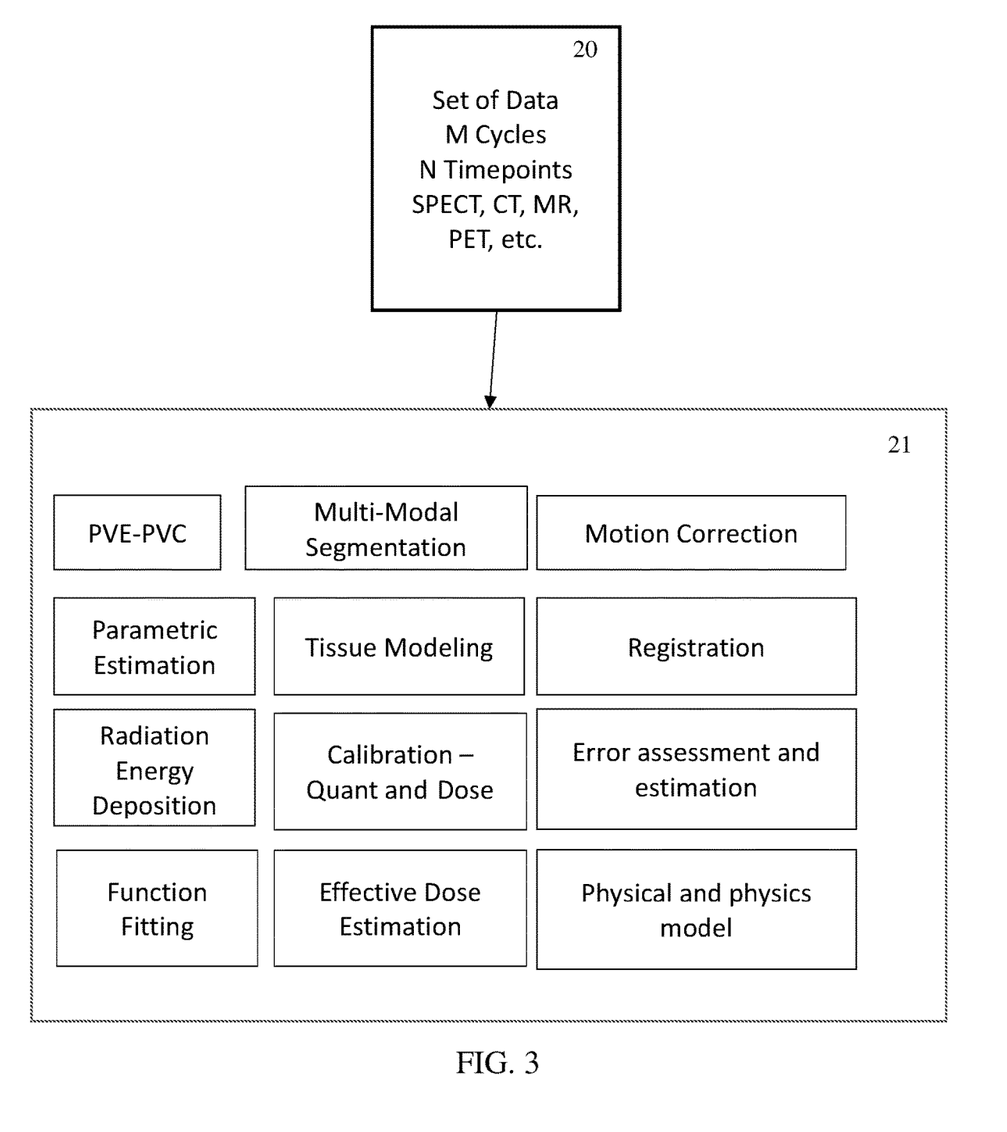
FIG. 3 illustrates example input and reconstruction.

FIG. 3 depicts the input of the set 20 of data from any number of M cycles, with N sets of emissions data for each of the cycles. Multi-modal, such as CT or MR data may be included in the input set 20. The image processor performs reconstruction 21 from the input set of data. For example, a reconstructed image or volume of dose is formed based on emission data of cycle 1 with two or more timepoints and CT images for each timepoint or one timepoint in the cycle.

For multi-modal reconstruction, a μ-map may be generated based on CT image and used to reconstruct the distribution from emission data. The segmentation map may be used to assist the reconstruction process. For example, the multi-modal reconstruction disclosed in U.S. Pat. No. 9,332,907 is used. The segment may be identified with EMI but IMI may be used. Different parametric models of tracer kinetics may be used, such as providing a different model for each different type of tissue identified by the segmentation.

In general, the uptake pattern is not of interest in voxels, but the uptake as means ($1^{st}$ moments) of the volumes of interest, such as organs or tumors, is of interest. The segmentation may be used to determine a distribution by organ or type of tissue. Segmentation drives tissue differentiation within the parametric model to better differentiate tissue properties, i.e. not only by HU but by density estimation. Voxel-based reconstruction may be used in other embodiments.

As represented in FIG. 3, the reconstruction 21 may include one or more various processes. For example, partial volume error or partial volume correction (PVE-PVC) may be used. The multi-modal reconstruction may be used. Motion correction may be used in reconstruction, such as for aligning the emission data (projections) and/or the aligning in the object domain. Registration may be used, such as registering the anatomical information with the emissions information. Tissue modeling, such as providing different parametric models for different tissue and/or tissue-based attenuation correction, may be used. The parametric estimation for the radiotracer kinetics is used where function fitting solves for the values of the variables in the parametric model using the emissions and/or object domain information over time. The dose distribution, or radiation energy deposition, is accounted for in the reconstruction. The imaging system and/or other processes are represented as physical or physics models in the reconstruction. The fit parametric model may be used to estimating the effective dose from the radiation energy deposition. The calibration weights may be used for uptake quantification and dose determination. The uncertainty or error may be assessed or estimated. Additional, different, or fewer processes may be used in reconstruction.

The fitting of the model in reconstruction or as part of the optimization to fit the object model to the detected emissions, uses the results of the calibration. The dose is adjusted based on the dose calibration. The estimation of dose in the reconstruction is based, in part, on the dose calibration. The estimated dose is cross-calibrated against accurate and traceably measured dose from phantoms.

The use of motion correction and partial volume estimation in performing the reconstruction provides for more accurate quantitative uptake and dose values. The partial volume estimation accuracy is also improved using information from the parametric model, which helps to differentiate tissue and organ borders. Alignment is performed using registration in image as well as projection domain to account for timepoint patient location differences, and motion correction is used to improve patient motion induced errors.

Returning to FIG. 2, in act 15, the image processor determines dose based on the model of pharmaceutical kinetics from the parametric model reconstruction. The dose, such as accumulated or effective dose, is determined as part of reconstruction. By solving for the fit of the model of radiopharmaceutical kinetics, the dose may be determined. The dose or biodose distribution is determined. The distribution is by voxel or tissue. For example, a mean dose for a volume of each structure of interest (e.g., type of tissue) is determined. The dose is directly reconstructed as part of performing the reconstruction.

In act 16, the image processor calculates uncertainty for the dose. The uncertainty in the dose estimation may be useful for planning margins and continued therapy. The risk to the patient may be minimized using the uncertainty information.

In one embodiment, the uncertainty is estimated as disclose in U.S. Pat. No. 9,364,192 or 2019/0168029. Statistical error computation estimates the accuracy of the quantitative values of uptake and dose. The error is propagated in a seamless way such that noisy voxels or regions at later times are stabilized. Dose, with or without dose uncertainty, is determined for each organ and/or voxel based on the corresponding systematic uncertainties and quantitative statistical uncertainties. A cumulative dose and dose uncertainty are determined for each organ and voxel. The cumulative and per-cycle dose and dose uncertainty may be presented in order to facilitate monitoring and/or modification of therapy.

Figure 4:
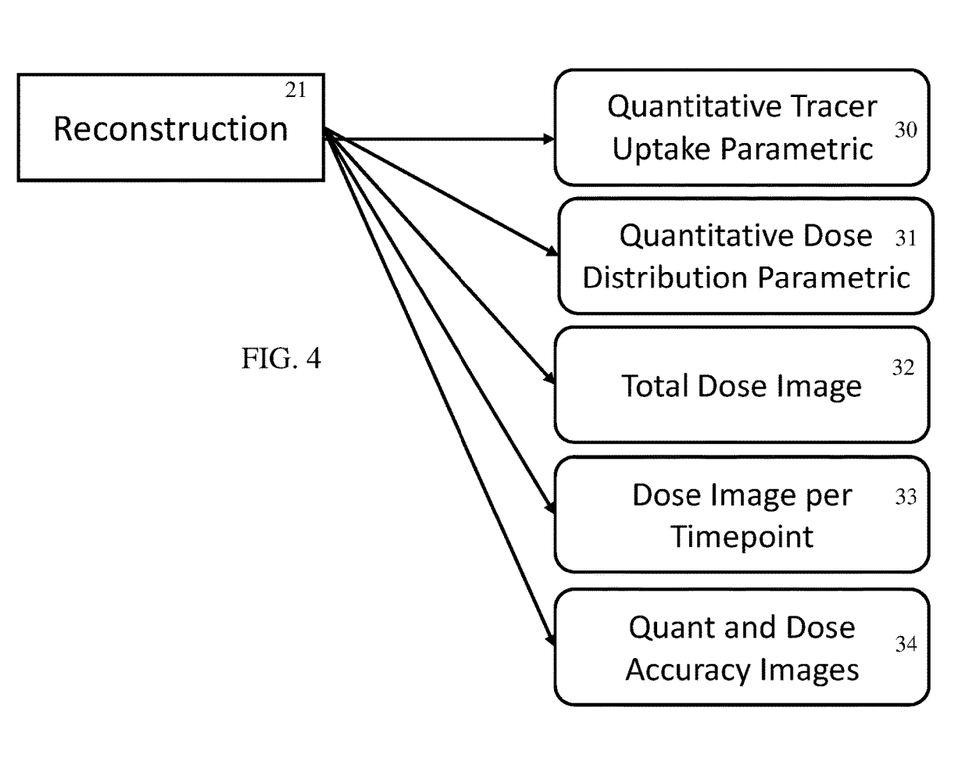
FIG. 4 illustrates example reconstruction and output.

FIG. 4 illustrates the outputs from the reconstruction 21. Quantiative uptake 30 for a given timepoint may be output. The quantitative dose 31 may be output as a distribution in 2D or 3D. The total dose 32, such as the accumulated dose during a given cycle, may be output. The accumulated dose 33 at each time point may be output. Quantification and/or dose accuracy 34 information may be output. Additional, different, or fewer outputs may be provided from the reconstruction 21.

Returning to FIG. 2, in act 17, the image processor generates an image of the dose output by the reconstruction. The output image object is of dose distribution at a particular time, for the cycle, up to the current time, up to the last scan, and/or predicted for the not-yet occurring end of cycle. The reconstruction outputs an image object or volume representing the dose in the patient from a last iteration of the optimization. This final image object is used for generating an image. The image object is a three-dimensional representation of the detected emissions, activity distribution, and/or dose of the patient. The resulting image is used for therapy planning.

The image object is rendered or otherwise used to generate an image. For example, a multi-planar reconstruction or single slice image of a plane is generated. The intersection of one or more planes with the image object is visualized. As another example, a surface or projection rendering is performed for three-dimensional imaging. Other imaging may be used.

One image is generated. Alternatively, a sequence of images is generated. For example, image objects of dose at different time periods are used to generate a sequence of images representing the dosing in the patient over time. Images may be generated for one or more of the different outputs shown in FIG. 4.

The dose image of the functional information from the reconstruction is displayed alone. Alternatively, an anatomical image is displayed with the functional image. For example, the functional image is overlaid on a CT image. The overlay may be dose colored for display on a gray scale CT image. Other combinations may be used, such as accumulated dose, uptake at a timepoint, and a CT image. An image of dose distribution and quantitative uptake may be generated and displayed.

For quantitative SPECT, the image may be an alphanumeric text of a dose value for a location. A graph, chart, or other representation of dose at multiple locations and/or times may be output. The spatial image representing distribution of dose may use color or brightness modulation to represent a level of dose by location. In one embodiment, the image is generated to show the average quantitative uptake by type of tissue.

The image may show the average quantitative uptake or dose by type of tissue. The tracer distribution and dose at any desired point in time may be shown. The uncertainty may also be displayed, such as showing uncertainty as a color, brightness level, alphanumeric text, or graph. An image of the accumulated or effective dose may be overlaid with information showing uncertainty.

The dose may be determined and displayed for any isotope, even fast decaying isotopes. Since the dose is estimated as part of reconstruction, the dose may be determined on the fly or during a given scan. The therapy may be adapted while the patient is lying on the table.

FIG. 5 shows one embodiment of a medical imaging system 50. The system 50 implements parametric model reconstruction. Sets of emission data from different timepoints or scans of the patient are used in one reconstruction to estimate the dose. The method of FIG. 2 or another method is implemented. By reconstructing the dose rather than time specific uptake or tracer distribution, the dose applied to the patient during a therapeutic cycle or over multiple cycles is provided for confirming dosage in therapy and/or planning further therapy.

The system 50 includes an image processor 56, an emission imaging system 52, anatomy imaging system 54, a memory 59, and a display 58. Additional, different, or fewer components may be provided. In one embodiment, the image processor 56, memory 59, and/or display 58 are part of one of the emission imaging system 52 or the anatomy imaging system 54. In alternative embodiments, the image processor 56, memory 59, and/or display 58 are provided as a workstation, server, or computer separate from the imaging systems 52, 54. The memory 59 is part of a computer or workstation with the image processor 56 or is a remote database, such as a picture archiving and communications system (PACS).

The anatomy imaging system 54 is a CT, MR, ultrasound, or other diagnostic medical imaging system. The anatomy imaging system 54 scans a patient with x-rays, ultrasound, or electric pulses to image the anatomy of the interior of the patient. A source transmits energy to the patient. A detector receives signals responsive to the transmitted energy. Any now known or later developed anatomy imaging system 54 may be used. While "imaging" is used herein, the anatomy imaging system 54 may be used to acquire anatomy data representing the patient without generating or displaying an image on a display device.

In one embodiment, the anatomy imaging system 54 is a CT system. An x-ray source and detector are mounted on a moveable gantry. The x-ray source generates x-rays, some of which pass through the patient. The detector detects the transmitted x-rays that pass through the patient. The energy used, timing, scan angles, and/or other aspects of the CT scan are set for a patient and used to scan a volume or other region of the patient. Computed tomography is used to generate a representation of the anatomy of the patient.

The emission imaging system 52 is any now known or later developed SPECT or PET scanner. The emission imaging system 52 includes a detector for detecting emitted radiation from within the patient. For SPECT, a gamma camera is used to detect. The detector detects photon emissions. The detector detects the photons. A given detector may detect a sequence of events from the same or different locations of the patient.

The emission tomography system 52 is configured by software, firmware, and/or hardware to detect emissions. The emission tomography system 52 detects emissions from the same patient but during different imaging sessions. Each imaging session provides a complete scan of the patient, such as positioning a gamma camera at different locations relative to the patient and detecting emissions at each position during a dwell time. The patient may leave the emission tomography system 52 (e.g., get up off of the bed) between the different imaging sessions. The imaging sessions may be performed at different periods over hours or days while the patient is being dosed by an internal radiopharmaceutical. The imaging sessions occur during a therapy cycle and/or over multiple therapy cycles. The imaging sessions may be over a period that is less than an entire cycle. For a same cycle, the patient is subject to therapy from a given application or dosage of a radiotracer during the different imaging sessions. For each cycle, a different application of the radiotracer is used.

The image processor 56 is a general processor, central processing unit, control processor, graphics processor, digital signal processor, application specific integrated circuit, field programmable gate array, amplifier, comparator, time-to-digital converter, analog-to-digital converter, digital circuit, analog circuit, timing circuit, combinations thereof, or another now known or later developed device for reconstructing a patient volume (i.e., object of the patient) from detected emissions. The image processor 56 is a single device or multiple devices operating in serial, parallel, or separately. The image processor 56 is specifically designed or provided for reconstruction but may be a main or general processor of a computer, such as a laptop or desktop computer, or may be a processor for handling tasks in a larger system. The image processor 56 may perform segmentation, reconstruction, uncertainty estimation, and/or image generation. The image processor 56 may perform other functions.

The image processor 56 is configurable. The image processor 56 is configured by software, firmware and/or hardware. Different software, firmware, and/or instructions are loaded or stored in memory 59 for configuring the image processor 56.

The image processor 56 is configured to reconstruct an object representing the dose applied to the patient. The dose is estimated from the detected emissions directly in parametric model reconstruction. The reconstruction may include zonal reconstruction, partial volume correction, motion correction, and/or other processes. For multi-modal or zonal reconstruction, the anatomical data from the anatomy imaging system 54 is used to segment or identify different zones or tissue types, which are then used in reconstruction. Alternatively, zonal reconstruction is not used.

The image processor 56 is configured to reconstruct a biodistribution of the dose from the radiotracer by fitting a parametric model of biological half-life of the radiotracer to the detected emissions. The radiotracer kinetics are modeled, such as including diffusion (e.g., k1 and k2 diffusion). The radiation transport and ionizing radiation energy deposition is modeled by a parametric model used in reconstruction. The parametric model may include Monte Carlo or dose kernels for emission determination. The generation of the object model from the emissions data uses, in part, the parametric model of the dose kinetics. The model may provide different values for variables for different types of tissue as fit in the reconstruction. Alternatively, different parametric models are used for different types of tissue. The segmentation may be used to select the parametric model used for reconstruction for each type of tissue to be represented.

The reconstruction may reconstruct the biodistribution of dose, based, at least in part, on calibration for the isotope of the radiotracer. The parametric model and/or imaging system model may include a variable for calibration, such as a weight. Different weights are provided for different isotopes and/or types of tissue.

The image processor 56 is configured to determine a dose from the parametric model. The fit parametric model outputs the dose based on the input detected emissions from different time points. The dose is output as an accumulated dose. The fit model may be used to determine the accumulated dose at any time. The reconstruction directly determines the dose, providing a biodistribution of dose.

The display 58 is a monitor, LCD, plasma, touch screen, printer, or other device for displaying an image for viewing by a user. The display 58 shows one or more images representing dose, such as accumulated dose at a given time for a cycle. Other images may be output, such as an image of function (i.e., representing the activity of the reconstructed object), such as uptake or activity concentration. The dose image is a quantitative image. The function image is a quantitative or qualitative SPECT or PET image. The image may be a volume rendering, a multi-planar reconstruction, a cross-section, and/or other image from a final image object. The image represents a distribution in the patient based on detected emissions from the emission imaging system 52.

The memory 59 is a random-access memory, graphics processing memory, video random access memory, system memory, cache memory, hard drive, optical media, magnetic media, flash drive, buffer, database, combinations thereof, or other now known or later developed memory device for storing data. The memory 59 stores detected emissions (e.g., PET or SPECT detected event data), signals from anatomy scanning (e.g., CT data), zone information, segmentation information, partial volume effect, smoothing filter coefficients, test activity, reconstructed activity, dose, biodistribution, calibration, and/or reconstruction information. The memory 59 stores data as processed, such as storing a segmentation, calibration, forward projection of the assigned test activities, reconstruction from detected emissions, image objects, dose, a rendered image, and/or other information.

The memory 59 or other memory is a non-transitory computer readable storage medium storing data representing instructions executable by the programmed image processor 56 for reconstruction. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for internal dose tomography, the method comprising:
   detecting first and second sets of emissions from a patient at first and second timepoints of a first radiopharmaceutical therapy cycle;
   performing tomographic, parametric model reconstruction from the first and second sets of emissions, the tomographic, parametric model reconstruction solving for a model of pharmaceutical kinetics as part of the reconstruction;
   determining dose based on the model of pharmaceutical kinetics from the parametric model reconstruction; and
   displaying the dose.

2. The method of claim 1 wherein detecting the first and second sets of emissions comprises detecting spatio-temporal inconsistent emissions with a single photon emission computed tomography scanner.

3. The method of claim 1 wherein detecting at the first and second timepoints of the first radiopharmaceutical therapy cycle comprises detecting from different scans separated by at least one hour after a first application of a radiopharmaceutical and before a subsequent application of the radiopharmaceutical.

4. The method of claim 1 wherein performing the tomographic, parametric model reconstruction comprises reconstructing from the first and second sets of emissions and a third set of emissions from a second radiopharmaceutical therapy cycle.

5. The method of claim 1 wherein performing the tomographic, parametric model reconstruction comprises performing with the parametric model for one segment of tissue of the patient with the one segment identified from extra-modal or intra-modal information.

6. The method of claim 1 wherein performing the tomographic, parametric model reconstruction comprises performing with the reconstruction for a third timepoint.

7. The method of claim 1 wherein performing the tomographic, parametric model reconstruction comprises solving for the model as a dynamic variation for wash-in and wash-out of a radiopharmaceutical.

8. The method of claim 1 wherein performing the tomographic, parametric model reconstruction comprises solving for the model as a dynamic variation for isotope and biological half-lives.

9. The method of claim 1 wherein determining the dose comprises determining as a mean for a volume of a structure of interest.

10. The method of claim 1 wherein determining the dose comprises directly reconstructing the dose as part of the performing.

11. The method of claim 1 further comprising calibrating for tissue density and isotope, and wherein performing comprises performing using results of the calibrating.

12. The method of claim 1 further comprises calculating uncertainty for the dose, and wherein displaying comprises displaying the dose and the uncertainty.

13. The method of claim 1 wherein performing comprises performing with motion correction and partial volume estimation.

14. A method for dose estimation from radiopharmaceutical therapy, the method comprising:
    parametrically estimating of quantitative uptake and dose distribution as part of parametric reconstruction from emissions of multiple timepoints corresponding to separate scans of separate imaging sessions;
    generating an image of the dose distribution and quantitative uptake.

15. The method of claim 14 wherein parametrically estimating comprises estimating with a model of tracer dynamics for biological dose efficacy.

16. The method of claim 14 wherein parametrically estimating comprises reconstructing with different parametric models for different types of tissue, and wherein generating the image comprises generating with the image showing average quantitative uptake by type of tissue.

17. The method of claim 14 wherein parametrically estimating the quantitative uptake comprises estimating based, in part, on dose calibration.

18. A medical imaging system comprising:
    an emission tomography system configured to detect emissions from the patient during different imaging sessions, the patient subject to therapy from a radiotracer during the different imaging sessions;
    an image processor configured to reconstruct a biodistribution of the radiotracer by fitting a parametric model of biological half-life of the radiotracer to the detected emissions and to determine a dose from the fit parametric model;
    a display configured to display the dose.

19. The medical imaging system of claim 18 wherein the parametric model includes radiation transport and ionizing radiation energy deposition by tissue type.

20. The medical imaging system of claim 18 wherein the image processor is configured to reconstruct the biodistribution based, in part, on a calibration for an isotope of the radiotracer.

* * * * *

UNITED STATES PATENT AND TRADEMARK OFFICE
CERTIFICATE OF CORRECTION

PATENT NO. : 11,524,178 B2
APPLICATION NO. : 16/845316
DATED : December 13, 2022
INVENTOR(S) : Alexander Hans Vija et al.

It is certified that error appears in the above-identified patent and that said Letters Patent is hereby corrected as shown below:

In the Specification

In the Detailed Description Section, Column 7, Line 22, "... kinitic parameters ..." should read "... kinetic parameters ..."

Signed and Sealed this
Twenty-ninth Day of October, 2024

Katherine Kelly Vidal
*Director of the United States Patent and Trademark Office*